United States Patent [19]

Chanas et al.

[11] Patent Number: 4,465,623

[45] Date of Patent: Aug. 14, 1984

[54] PROTHROMBIN COMPLEX CONCENTRATES, PREPARATION AND APPLICATION THEREOF

[75] Inventors: Maryse Chanas, Sainte-Foy-les-Lyon; Jacques Liautaud, Limonest; Jean Pla, Sainte-Foy-les-Lyon, all of France; Edward Shanbrom, Santa Ana, Calif.

[73] Assignee: Societe Anonyme dite: Institut Merieux, Lyons, France

[21] Appl. No.: 476,126

[22] Filed: Mar. 17, 1983

Related U.S. Application Data

[63] Continuation of Ser. No. 227,041, filed as PCT FR 80/00069, published as WO 80/02426, Nov. 13, 1980, §102(e) date Dec. 29, 1980, abandoned.

[30] Foreign Application Priority Data

May 4, 1979 [FR] France .................................. 79 11272

[51] Int. Cl.³ ....................... C07G 7/00; C07G 17/00; A61K 35/16
[52] U.S. Cl. ............................... 260/112 B; 424/101; 424/177
[58] Field of Search ..................... 260/112 B; 424/101

[56] References Cited

U.S. PATENT DOCUMENTS 3,560,475  2/1971  Fekete et al. .................. 260/112 B
4,087,415  5/1978  Bick et al. ..................... 260/112 B
4,411,794 10/1983  Schwinn et al. ............ 260/112 B X

FOREIGN PATENT DOCUMENTS 2001528  2/1979  United Kingdom .

OTHER PUBLICATIONS

Blood, vol. 49, No. 2, Feb. 1977, pp. 159–170, White et al.
Thromb. Diath. Haemorrh., 1972, 27(3), pp. 490–501, Swart et al.
Chem. Abs. 77:124372g, 1972, Swart et al.
Chem. Abs. 77:137016u, 1972, Wickerhauser et al.
Chem. Abs. 86:127141c, 1977, White et al.
Thromb. Res. 1978, 12(4), 571–582, Chandra et al.

*Primary Examiner*—Howard E. Schain
*Attorney, Agent, or Firm*—Cushman, Darby & Cushman

[57] ABSTRACT

Procedure for the preparation of a concentrate of prothrombinogenic compound.

This procedure, in which, starting from a source of prothrombinogenic compound, an adsorption is followed by an elution, is characterized by the fact that a source of prothrombinogenic compound and a source of antithrombin III (or AT III) is placed in contact with an adsorbing agent capable of adsorbing both the prothrombinogenic compound and antithrombin III, and that the foregoing occurs in the presence of heparin, at least during the elution stage, and that elution is carried out with an elution agent capable of eluting the prothrombinogenic compound, the AT III and heparin at the same time.

Application of the product obtained, notably to the treatment of blood coagulation difficulties.

14 Claims, No Drawings

PROTHROMBIN COMPLEX CONCENTRATES, PREPARATION AND APPLICATION THEREOF

This is a continuation, of application Serial No. 227,041, filed as PCT FR 80/00069, published as WO 80/02426, Nov. 13, 1980, § 102(e) dated Dec. 29, 1980, now abandoned.

The present invention relates to a procedure for the preparation of a factor IX concentrate or, more generally, a concentrate of a prothrombinogenic compound, in a highly purified form, as well as to the new, highly purified concentrates of prothrombinogenic compound which may be obtained thanks to said procedure.

Various prothrombinogenic compound preparation tests (for compound containing coagulation factors II, VII, IX and X) have already been proposed for the treatment of various coagulation disorders, attributable principally to factor IX deficiencies (hemophilia B) or to hepatic insufficiency.

Accordingly, efforts have been made to purify the prothrombinogenic compound starting from fresh or freshly-frozen plasma by using calcium phosphate or DEAE ion exchangers.

Other procedures have also been used, such as adsorption on barium sulfate or alumina gel.

Also proposed previously was the preparation of a factor IX concentrate starting from Cohn's fraction III resulting from the fractioning of freshly frozen plasma by ethanol when cold.

These various products have proved to be unstable because certain coagulation factors are in them in the "activated" state, with the result that some 11 percent of the patients treated with these concentrates have developed thromboses.

To remedy these drawbacks, Mr. Wickerhauser has already taken steps to inactivate the activated factor IX present in Cohn's fraction III by adding heparin and its cofactor, obtained separately from Cohn's fraction IV, to the concentrate obtained after elution.

As a result, an International Committee has formally recommended that less dangerous preparations be developed for the addition of heparin to the final product so as to avoid the harmful effects of the anticoagulant activity.

Other procedures have also, once the product has been obtained, called for its stabilization by adding heparin and its cofactor, this by using, for example, a complete serum as the source for the heparin cofactor.

However, the concentrates currently being proposed have a significant proportion of activated factor despite the final addition of heparin.

The present invention proposes to furnish a procedure for the preparation of a prothrombinogenic compound which makes it possible directly to obtain a non-"activated" concentrate which is, in other words, stable and without risk for patients.

Another purpose of the invention is to furnish a procedure for obtaining such a concentrate which is simple and inexpensive.

The subject of the invention is a procedure for the preparation of a prothrombinogenic compound concentrate in which, starting from a source of prothrombinogenic compound, an adsorption is followed by an elution, characterized by the fact that a source of prothrombinogenic compounds and a source of antithrombin III (or AT III) are put into contact with an adsorbing agent capable of adsorbing both the prothrombinogenic compound and antithrombin III, and that the foregoing occurs in the presence of heparin, at least during the elution stage, and that elution is carried out with an elution agent capable of eluting the prothrombinogenic compound, AT III and heparin at the same time.

Heparin activates antithrombin III. The activated antithrombin III protects and stabilizes the prothrombinogenic compound.

In the event that the prothrombinogenic compound source contains AT III, in sufficient quantity, the two initial sources are obviously confused into one.

In the event that the prothrombinogenic compound source contains no AT III or contains an amount of it which is insufficient to stabilize said compound, it is appropriate to add a sufficient amount of AT III before elution. Preferably, the AT III is added to the prothrombinogenic compound source before adsorption.

Heparin is added before elution. In other words, it is possible to add heparin to the eluting agent, after which elution is carried out. But preferably, heparin is added to the prothrombinogenic compound source or to the AT III source before adsorption. The heparin can also be placed in contact with the adsorbing agent, and the latter is then placed in contact with the initial source(s).

When it is necessary to add AT III to the prothrombinogenic compound source, said addition is preferably carried out at the same time the heparin is added.

Accordingly, in the preferred implementation mode of the procedure, the prothrombinogenic compound is protected throughout the complete duration of the procedure.

As the initial source, it is preferable to use the fraction obtained from unfrozen plasma after the elimination of the cryoprecipitate, the so-called "cryo poor plasma" fraction or CPP.

However, fresh plasma, frozen or unfrozen, may also be used.

Cohn's fraction III may also be used as an initial product, to which it is advisable to add antithrombin AT III, for instance in the form of Cohn's fraction IV. One can also use, alone, fraction IV as an initial product, since said fraction IV is also a prothrombinogenic compound source.

It is preferable when starting from plasma to add the heparin as soon as possible, even, if possible, before freezing.

The amount of heparin to be added depends on the quality of the source of prothrombinogenic compound. This amount generally varies from 0.1 to 1 U.I. more or less per ml of source.

The adsorption may be carried out on alumina gel, which has proved particularly suited to the adsorption and subsequent elution of the protected prothrombinogenic compound in accordance with the invention.

However, other adsorbing agents may be used provided that they are able to adsorb the concentrate and the cofactor (AT III) activated by heparin.

The adsorption is carried out at the most favorable temperature, which depends principally on the nature of the adsorbing agent. Generally a temperature below the ambient temperature is used, for example from 0° to 15° C. Accordingly, for the alumina gel the temperature is preferably between about 2° and 8° C.

The elution is carried out with any agent capable of eluting simultaneously the prothrombinogenic compound and AT III. Generally used is a buffer with suitable ionic force.

In accordance with a particular mode of execution, the source, for example a CPP fraction to which heparin has been added, is adsorbed on alumina gel, following which elution is carried out between 0° C. and the ambient temperature.

The eluted fraction may be purified to about pH 7 by one or several additions of polyethylene glycol (PEG) (5-10 percent), which precipitates the undesirable proteins. Preferably the PEG precipitations are carried out at temperatures below the ambient temperature, at 0°-8° C. for example, particularly at about 2°-4° C.

After eliminating the precipitate of contaminant proteins by means of centrifuging, the pH of the supernatant is adjusted to a value ranging from 4.8 to 5.2, PEG is added to a concentration of 12 to 20 percent and the precipitate containing the prothrombinogenic compound is isolated. This precipitation is also carried out at low temperature. The prothrombinogenic compound obtained is then redissolved, and the final solution eventually undergoes the filtration, distribution and lyophilization operations.

The subject of the invention also covers a prothrombinogenic compound concentrate characterized by the fact that it is practically free of activated prothrombinogenic compound. Such a concentrate may be obtained by the procedure referred to above. It is distinguished from the products heretofore obtained which generally contain substantial or extremely high proportions of compound in the "activated" state.

The concentrate of prothrombinogenic compound according to the invention may be used as a medication, particularly for the treatment of coagulation problems, in particular deficiencies of factor IX but also hemorrhagic illnesses of the newborn, overdoses of coumarin-based medicines, and liver diseases in the advanced state. It is administered in accordance with customary methods and posologies.

This compound has the customary pharmacological properties and harmlessness of the other concentrates of purified prothrombinogenic compounds, but is distinguished from them notably by the absence or near absence of undesirable thrombotic complications.

The invention will now be described in greater detail with the help of a nonlimitative example of its application.

The initial source is the fraction known as CPP, i.e., the fraction remaining from a frozen plasma which has been thawed and from which the cryoprecipitate has then been eliminated.

Heparin is added to this fraction so as to have a mixture of about 0.5 unit per milliliter of plasma CPP.

Then, at a low temperature between 0° and 8° C., and preferably between 2° and 4° C., adsorption is carried out on an alumina gel at the rate of 10 to 20 milliliters of alumina gel per liter of heparined plasma.

Stirring is followed by centrifuging; the gel is retained.

The gel is then eluted with the help of a standard and appropriate eluting buffer. For instance, use may be made of a buffer consisting of 0.25 M of potassium phosphate, 0.17 M of trisodium citrate, 5 $H_2O$—and 0.003 M of EDTA. The pH is adjusted to the range of 7.5 to 8.5 and elution can be carried out with a volume of buffer on the order of one thirtieth the volume of the plasma CPP. The elution is carried out in the customary manner by putting the gel in suspension in the eluting buffer and stirring. Centrifuging follows and the eluate is retained.

The pH of the eluate is then adjusted to about 7 and the temperature to about 2° to 4° C., following which 5 to 10 percent is added by weight/volume of PEG (polyethylene glycol). Stirring follows, after which there is centrifuging, and the precipitate is eliminated so as to keep the supernatant.

The pH of the supernatant is then lowered to a relatively low value on the order of 4.8 to 5.2, PEG is added until a 12 to 20 percent PEG content is reached, taking into account the PEG added initially and the increase in volume, this is followed by stirring and centrifuging and the precipitate is retained. This stage is also carried out at a low temperature.

The precipitate is then redissolved, preferably at ambient temperature, in a solution containing, for example, sodium chloride or trisodium citrate, the volume of dissolution being about ½ or 1/3 the volume of the eluate. After dissolving, the pH is adjusted until the solution is made clear, indicating complete dissolving, which occurs in the vicinity of pH 7.

Filtering must then be carried out, preferably membrane filtering, with the final filtering at least being carried out under sterile conditions.

The product obtained is then sterilely distributed into the desired aliquot portions and then lyophilized, this immediately after freezing.

This yields a factor IX concentrate which has practically no undesirable activity.

The example just described is obviously in no way limitative.

The lyophilized concentrate is administered parenterally. The concentrate is nontoxic at customary active dosage levels.

The subject of the invention is also a procedure for treating coagulation problems, characterized by the fact that a person suffering from said problems is administered an effective quantity of a concentrate of prothrombinogenic compound as defined in the present application.

We claim:

1. A process for preparing a prothrombinogenic complex concentrate essentially free of activated prothrombinogenic complex comprising contacting a source of prothrombinogenic complex comprising prothrombinogenic complex and antithrombin III with, as an adsorbing agent, alumina gel, in the presence of heparin so that said source and said heparin are adsorbed thereon, and thereafter eluting simultaneously said source and said heparin from said adsorbing agent, said eluting being carried out with a buffer solution at a pH of 7.5-8.5.

2. The process of claim 1 wherein said source comprises a fraction of plasma obtained after the elimination of cryoprecipitate therefrom.

3. The process of claim 1 wherein said source comprises fresh plasma.

4. The process of claim 1 wherein said source comprises Cohn's fraction IV.

5. The process of claim 1 which includes adding heparin to said source prior to contacting said source with said adsorption agent.

6. The process of claim 1 wherein said heparin is present in an amount ranging from about 0.1 to 1 I.U. per ml. of said source.

7. The process of claim 1 wherein said contacting step is carried out at a temperature lower than ambient temperature.

8. The process of claim 7 wherein said contacting step is carried out at a temperature ranging from 0° to 15° C.

9. The process of claim 7 wherein said contacting step is carried out at a temperature ranging from 2° to 8° C.

10. The process of claim 1 wherein the eluting step is carried out at a temperature ranging from 0° C. to ambient temperature.

11. The process of claim 10 wherein the eluting step is carried out at ambient temperature.

12. The process of claim 1 which includes, subsequent to the eluting step, purifying the resulting eluate with polyethylene glycol at a pH of about 7 and at a temperature lower than ambient temperature so as to precipitate undesirable proteins therefrom.

13. The process of claim 12 which also includes removing said precipitate, adjusting the pH of the resulting supernatant to 4.8 to 5.2 and thereafter adding sufficient polyethylene glycol to precipitate said prothrombinogenic complex concentrate.

14. A process for preparing a prothrombinogenic complex concentrate essentially free of activated prothrombinogenic complex comprising contacting a source of prothrombinogenic complex comprising prothrombinogenic complex and antithrombin III present in an amount sufficient to stabilize said prothrombinogenic complex with, as an adsorbing agent, alumina gel, in the presence of heparin so that said source and said heparin are adsorbed thereon, eluting simultaneously said source and said heparin from said adsorbing agent, said eluting being carried out with a buffer solution at a pH of 7.5–8.5, purifying the resulting eluate with polyethylene glycol at a pH of about 7 and at a temperature lower than ambient temperature so as to precipitate undesirable proteins therefrom, removing said precipitate, adjusting the pH of the resulting supernatant to 4.8 to 5.2 and thereafter adding sufficient polyethylene glycol to precipitate said prothrombinogenic complex concentrate.

* * * * *